United States Patent
Stöbener et al.

(10) Patent No.: US 12,403,426 B2
(45) Date of Patent: Sep. 2, 2025

(54) ISOTOPE RATIO MEASUREMENT

(71) Applicant: Thermo Fisher Scientific (Bremen) GmbH, Bremen (DE)

(72) Inventors: Nils Stöbener, Bremen (DE); Jens Radke, Bremen (DE); Johannes Schwieters, Bremen (DE); Holger Jeglinski, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 457 days.

(21) Appl. No.: 18/076,806

(22) Filed: Dec. 7, 2022

(65) Prior Publication Data
US 2023/0108163 A1 Apr. 6, 2023

Related U.S. Application Data

(62) Division of application No. 16/526,646, filed on Jul. 30, 2019, now Pat. No. 11,583,805.

(30) Foreign Application Priority Data

Aug. 7, 2018 (DE) .................. 18187852.1

(51) Int. Cl.
*H01J 49/00* (2006.01)
*B01D 59/44* (2006.01)
(Continued)

(52) U.S. Cl.
CPC ............ *B01D 59/44* (2013.01); *G16C 20/20* (2019.02); *H01J 49/0009* (2013.01); *H01J 49/0422* (2013.01)

(58) Field of Classification Search
CPC ..... B01D 59/44; G16C 20/20; H01J 49/0009; H01J 49/0422; H01J 49/0027; G01N 27/62; G01N 21/31
(Continued)

(56) References Cited

U.S. PATENT DOCUMENTS

| 6,078,049 A | 6/2000 | Schäfer et al. |
| 8,402,814 B2 | 3/2013 | Hatscher et al. |

(Continued)

FOREIGN PATENT DOCUMENTS

| CN | 105659354 A | 6/2016 |
| CN | 106226383 A | 12/2016 |

(Continued)

OTHER PUBLICATIONS

Brenna et al., "High-Precision Continuous-Flow Isotope Ratio Mass Spectrometry," Mass Spectrometry Reviews 16(5):227-258, Sep.-Oct. 1997.

(Continued)

*Primary Examiner* — Michael Maskell
(74) *Attorney, Agent, or Firm* — Klarquist Sparkman, LLP

(57) ABSTRACT

An isotope ratio spectrometer is operated for measurement of a sample. First isotope ratios and first signal intensities are measured for a reference in the spectrometer, over a first measurement time period. A first relationship comprising a relationship between the first isotope ratios and the first signal intensities is determined. Sample isotope ratios and sample signal intensities are measured in the spectrometer, over a second measurement time period subsequent to the first measurement time period. Second isotope ratios and second signal intensities for a reference are measured in the spectrometer, over a third measurement time period subsequent to the second measurement time period. A second relationship comprising a relationship between the second isotope ratios and the second signal intensities is determined. A reference isotope ratio is estimated for a time X within the second measurement time period, based on the first relationship and the second relationship.

18 Claims, 4 Drawing Sheets

(51) Int. Cl.
*G16C 20/20* (2019.01)
*H01J 49/04* (2006.01)

(58) Field of Classification Search
USPC .................................................. 250/281, 282
See application file for complete search history.

(56) References Cited

U.S. PATENT DOCUMENTS

| | | |
|---|---|---|
| 8,969,791 B2 | 3/2015 | Mukaibatake |
| 9,766,219 B2 | 9/2017 | Wapelhorst et al. |
| 10,234,381 B2 | 3/2019 | Koulikov |
| 10,615,016 B2 | 4/2020 | Eiler et al. |
| 2009/0314057 A1 | 12/2009 | Hatscher et al. |
| 2014/0361159 A1 | 12/2014 | Pfaff et al. |
| 2015/0187556 A1 | 7/2015 | Shimura et al. |
| 2016/0061798 A1 | 3/2016 | Wapelhorst et al. |
| 2016/0266031 A1* | 9/2016 | Schlueter ........... G01N 33/0006 |
| 2019/0074169 A1 | 3/2019 | Eiler et al. |
| 2020/0355654 A1 | 11/2020 | Hobby et al. |

FOREIGN PATENT DOCUMENTS

| | | |
|---|---|---|
| EP | 2874177 A1 | 5/2015 |
| WO | WO 2015/067806 A1 | 5/2015 |

OTHER PUBLICATIONS

Chinese Office Action issued on Oct. 20, 2021, for Chinese Application No. 201910726732.1.

Hu et al., "A modified procedure for gas-source isotope ratio mass spectrometry: The long-integration dual-inlet (LIDI) methodology and implications for clumped isotope measurements," Rapid Communications in Mass Spectrometry 28(13):1413-1425, May 22, 2014.

* cited by examiner

ISOTOPE RATIO MEASUREMENT

CLAIM TO PRIORITY

This application claims the benefit of European patent application no. EP18187852.1, entitled "Isotope Ratio Measurement," by Stöbener et al., and filed on Aug. 7, 2018. This application is a also a divisional of U.S. Ser. No. 16/526,646, filed Jul. 30, 2019. The content of the above-identified applications are incorporated herein by reference in their entirety.

TECHNICAL FIELD OF THE DISCLOSURE

The disclosure concerns a method for operating an isotope ratio spectrometer for measurement of a sample, a computer program for controlling an isotope ratio spectrometer in accordance with a method and an isotope ratio spectrometer configured accordingly.

BACKGROUND TO THE DISCLOSURE

Isotope-ratio analysis is used to measure the relative abundance of isotopes (isotope ratio) in a sample, which may be solid, liquid or gaseous and for a wide variety of elements. From each sample, a sample fluid can be generated by a known process, preferably a sample gas. For instance, it is used for determining the isotope ratios $^{13}C/^{12}C$ and/or $^{18}O/^{16}O$ from $CO_2$, such as in air. Isotope-ratio analysis is most commonly performed by mass spectrometry (MS) but may also be performed by optical spectrometry.

For optical spectrometry, an isotope ratio is generally determined in a measurement cell of the spectrometer by measuring two separate spectral absorption lines, typically in the infrared region, one line for each different isotopic species (isotopologue), e.g. an absorption line for $^{12}C^{16}O_2$ and another line for $^{13}C^{16}O_2$. A convenient absorption line for $CO_2$ is the line at or about 4.3218 μm. If more lines are available per isotope (e.g. a doublet or triplet) it is possible to measure and use the information from more than one line, e.g. for other gases than $CO_2$ or in other spectral ranges that might be interesting. The ratio of the intensities of the spectral absorption lines is a measure of the ratio of the abundance of each of the isotopic species (and hence the isotope ratio, e.g. $^{13}C/^{12}C$. The outputs of the spectrometer are thus ratios of different isotopic lines (e.g. $R_{13C}=c_{13c}/c_{12c}$). The result is referenced against international standards using the established delta notation for isotope ratio reporting (e.g. $\delta_{13c}[‰]$).

A general review of isotope ratio mass spectrometry (IRMS) and gas inlet systems can be found in Brenna et al, Mass Spectrometry Reviews, 1997, 16, 227-258.

In IRMS, a sample is normally measured against a working standard, that is, one or more references, preferably reference fluids and in particular reference gases, of known isotopic ratio. To allow this, the spectrometer is equipped with a dual inlet (DI) system. A sample gas (e.g. $CO_2$) is provided from a high vacuum bellow or, alternatively, from a sample preparation device (such as the Kiel IV marketed by Thermo Fisher Scientific Inc.) via a thin capillary to the inlet of the mass spectrometer. A reference gas of the same chemical composition as the sample is administered to the inlet via a second thin capillary from a high vacuum bellow. This reference gas allows normalization, by attributing standardized values of isotope ratios to the measured raw isotope ratios of the sample gas (so-called "delta" notation).

In an isotope ratio mass spectrometer, the signal from detected ions of a specific mass-to-charge (m/z) ratio (sometimes designated simply as "mass", assuming that that charge of the ions, z, is 1), does not increase in the same way with increasing partial pressure of the sample as the signal from detected ions of a different mass-to-charge ratio. This non-linearity of IRMS results in a dependency of the detected isotope ratios on the partial pressure of the investigated ions, which can be observed for reference gases, for example. It will understood that, physically, the isotope ratios of the investigated ions will be the same, irrespective of (or independent from) the partial pressure of the sample. It is only the detected signal that changes. However, reference gases have standardized, pressure-independent values of isotope ratios and this information can be used for standardization purposes.

In well-known ("classical") DI measurements, the sample and reference gases are measured alternately for short integration time intervals (up to 30 seconds). This allows correction of any instrumental drift, by comparing each sample interval with two reference intervals (taken before and after the sample measurement). Assuming a linear change of the measured isotope ratios over time, a hypothetical isotope ratio of the reference at the time of the sample measurement can be calculated from the reference intervals before and after the sample interval (known as "bracketing"). However, the non-linearity of IRMS requires sample and reference isotope ratios to be measured at the same partial pressure in the ion source. With such well-known DI techniques, this is achieved by measuring the signal intensity for a specific mass-to-charge ratio of the sample immediately before the first measurement of the reference gas and to use this signal intensity to adjust the reference gas pressure such that the same signal intensity is reached for the reference gas. The signal intensity is dependent on the gas flow into the ion source and, therefore, on present pressure, which can be adjusted if a bellow is used. Due to the finite amount of sample and reference gases available, the respective gas pressures and, hence, the signal intensities decrease during the measurement. This is acceptable as long as the signal intensity at the beginning of the measurement and their further decrease is comparable for sample and reference, thereby allowing the comparison of isotope ratios measured at the same or similar intensity. For any device, in which the sample gas is in a micro volume, the sample gas pressure and/or reference gas pressure may be only adjustable, if a sufficient quantity of pure reference or sample gas can be provided to the micro volume (for example, from a bellow with 100 mL 100% $CO_2$ at 80 mbar, 8000 Pa). Otherwise the sample gas might be already consumed during the pressure adjustment.

Measured isotope ratios for the sample and reference gases at the same concentration and at close time intervals can therefore be used in the well-known DI measurements to determine the deviation of the isotope ratio of the sample gas from the standard isotope ratio, to apply the "delta" notation. An example of a calibration procedure to match the concentration of a sample gas and the standardized reference gas for a continuous flow gas isotope ratio spectrometer (having only one inlet or capillary to the analyser) is described in International Patent Application Publication Number WO2015/067806 and US patent publication 2009/314057 A1.

Long Integration Dual Inlet (LIDI) is a more recent variant of DI where sample gas and reference gas are not measured alternately over relatively short time durations, but rather a longer uninterrupted sample measurement (typically of about 600 seconds) is taken, with a single reference gas measurement taken subsequently. This allows better sample utilization, especially when limited sample volume is available or when a rare species is to be measured, requiring highest precision. The pressure of the sample gas may be similar as for classical DI measurements at the beginning of the sample measurement. A typical sample size for "clumped" isotopologue (47-$CO_2$) measurement would be 100 µg $CaCO_3$, corresponding to 20 µL $CO_2$ at ambient pressure. Normally, LIDI is applied for the measurement of a finite amount of sample gas from a micro-volume acting as a reservoir. The sample gas is measured against a reference gas provided by a second micro-volume in this case. Examples of existing LIDI IRMS instruments include the MAT 253 and MAT 253 Plus, marketed by Thermo Fisher Scientific, Inc.

LIDI has especially been proposed for the measurement of the "clumped" isotopologue $^{13}C^{18}O^{16}O$, named 47-$CO_2$, which carries heavy isotopes ($^{13}C$, $^{18}O$) on two positions. While the abundancy of clumped isotopologues can be calculated stochastically from the relative proportion of $^{13}C$ and $^{18}O$ present in a $CO_2$ sample, a deviation from this theoretical value is usually observed. This is due to the fact that the formation of the clumped isotopologues of $^{13}C^{18}O^{16}O$ is thermodynamically favoured over isotopologues featuring just one heavy isotope. Since the degree of the deviation between expected and observed abundancy is solely dependent on the temperature at which the $CO_2$ or carbonate mineral was formed, precise measurement of the $^{13}C^{18}O^{16}O$ abundancy can be used to reconstruct these temperatures and, hence, the climate of the past. As the relative abundancy of $^{13}C^{18}O^{16}O$ is in the order of $10^{-5}$, long integration times with optimal sample utilization are desirably applied to achieve sufficient precision. A more detailed description of the LIDI workflow and its application with clumped isotopologues can be found in "A modified procedure for gas-source isotope ratio mass spectrometry: the long-integration dual-inlet (LIDI) methodology and implications for clumped isotope measurements", Hu et al., Rapid Commun. Mass Spectrom. 2014, 28, pp. 1413-1425.

Performing bracketing as described for "classical" DI is not possible with LIDI. In view of the limited volume of sample available, taking an initial measurement of the sample intensity before a first reference gas measurement would be impractical and potentially impossible due to the high consumption of the associated sample. The partial pressure of the sample gas is reduced over time. Without an initial measurement of the sample intensity, first measurement of the reference gas at the same intensity is not possible, preventing bracketing in existing LIDI systems. As a result, existing LIDI systems compare each set of sample measurements (that is, one sample run) to one set of reference measurements (one reference run) only, which is measured after the sample measurements are taken. Provided the instrument drift is sufficiently under control, the accuracy of the calibrated measurements is maintained. Change in ambient temperature is typically the most significant cause for instrumental drift. Control of this can often only be achieved with appropriate environmental conditions in the instrument's place of operation (such as a laboratory).

A further issue arises with LIDI systems. As the sample gas is rapidly consumed during the measurement, partial pressure of the sample gas and accordingly its signal intensity decreases over the time of sample measurement. Due to the nonlinearity of IRMS, the observed isotope ratios will therefore also change during the course of the measurement. This is acceptable, as long as the intensities for sample and reference at the beginning of their respective measurements are precisely the same and the change in isotope ratio is the same for both sample and reference gases, that is, the decay of the signal intensities is the same.

To match the sample intensities, the partial pressure of the reference gas may be adjusted to achieving matching of the measured intensity of the sample. However, this prevents the measurement of a reference gas prior to the sample and at matched intensities. To achieve the same decay in signal intensities, the gas flow for sample and reference through the respective capillaries are desirably kept the same. This is effected by closing down the inner diameter of the capillaries by external compression (crimping). The procedure to "match" these capillaries is quite laborious and rarely delivers perfect results. The outcome is also dependent on the actual size of the micro-volumes used for sample and reference, causing further mismatch between sample and reference intensity decays. As a result of all these issues, the application of bracketing to LIDI has not been considered possible.

Therefore, it is desirable to implement LIDI with improved referencing, especially to deal with instrumental drift and mitigate issues arising from the nonlinearity of IRMS.

SUMMARY OF THE INVENTION

Against this background, there is provided: a method of operating an isotope ratio spectrometer for measurement of a gaseous sample; a computer program; and an isotope ratio spectrometer. Further features of the invention are detailed in the dependent claims and discussed herein.

It has been recognised that, instead of matching sample and reference intensities physically during the measurement (which is challenging for LIDI), the matching may be done after a measurement process, for example as a part of the data evaluation. Reference gas measurements are made before and after the sample gas measurement (although in some implementations, only one may be required). Each reference gas measurement typically has a time duration (a first measurement time period) of the same length as a time duration of the sample gas measurements (a second measurement time period), but optionally the time duration of the reference gas measurements may be longer than the time duration of the sample gas measurements (the length of the time duration of the sample gas measurements may be at least or no more than 0.2, 0.3, 0.4, 0.5, 0.6, 0.7, 0.8, 0.9 or 1 times the length of the time duration of each or both of the reference gas measurements). Relationships (for example, by a function or a table) between the measured isotope ratio and signal intensity for the reference gas measurements are determined for the reference gas measurement periods. Using these relationships, isotope ratios for any signal intensity of the reference gases (preferably within or around a range of signal intensities measured for the reference gases) can be determined. This allows instrumental drift to be estimated and one or more reference gas isotope ratios for during the sample gas measurement can be evaluated. In this way, matching of the sample gas and reference gas measurements can be applied, even though the sample gas and reference gas may be measurement at significantly different times. A form of bracketing can thereby be achieved. This is especially powerful for LIDI IRMS, but can also be used for classical DI IRMS, in particular in IRMS where there is a pronounced decay in signal intensity during measurement of sample gases and typically also reference gases. In another embodiment only the signal intensity of the sample gas is decreasing and the pressure of the reference gas might be controlled in a manner such that it is increasing in at least one of the time periods of the reference gas measurements. Although this disclosure generally focuses on gas measurements, it will be understood that this can more generally be applied to measurement of any kind of samples, which can be analysed in fluid (gas and/or liquid) form. The fluid form may be the sample itself or generated from the sample by known processes.

Any of the methods herein disclosed may be implemented as software, for example as a computer program, configured when operated by a processor to control an isotope ratio spectrometer. Additionally or alternatively, programmable hardware, firmware or other type of processor, controller or data device may be used. Such a device can be connected to a processor of an isotope ratio spectrometer by any kind of data and/or network transmission, including by a cloud infrastructure, for example. An isotope ratio spectrometer configured to operate in accordance with the disclosure is also provided.

As an example of the disclosed method, first isotope ratios and first signal intensities (typically for a main or most common isotope, but alternatively for a minor or rare isotope) may be measured for a first reference gas in an isotope ratio spectrometer, such as a LIDI system. This is done over a first measurement time period. A first relationship comprising a relationship between the first isotope ratios and the first signal intensities is determined or derived from the obtained data. Sample gas isotope ratios and sample gas signal intensities (typically for a main or most common isotope, but alternatively for a minor or rare isotope) are further measured in the spectrometer over a second measurement time period, subsequent to the first measurement time period. The sample and/or reference gases may be provided from a reservoir comprising a finite volume (such as a micro-volume or a sample preparation device). In some embodiments, the sample and/or reference gases are released from a solid sample in a (dedicated) sample preparation device, for example a reference gas may be released from a Standard Reference Material (SRM) in such a device. In a third measurement time period that is subsequent to the second measurement time period, second isotope ratios and second signal intensities are measured for a second reference gas (of the same chemical composition as the first reference gas) in the spectrometer and a second relationship comprising a (mathematical) relationship between the second isotope ratios and the second signal intensities is determined. Then, a reference gas isotope ratio for a time X within the second measurement time period is estimated, based on the first relationship and the second relationship. This technique can potentially allow for mathematical intensity matching between the reference gas and sample gas and can be used for classical DI or LIDI. Intensity matching can be useful even in the absence of instrumental drift, for example in classical DI, if the matching of the capillaries for the sample and reference gases is not perfect or when a pronounced non-linearity is present during the integration of a classical DI measurement. A sample gas isotope ratio measured at the time X may thereby be normalized using the estimated reference gas isotope ratio for the time X.

The relationship between the first isotope ratios and the first signal intensities and/or the relationship between the second isotope ratios and the second signal intensities may be non-linear. Optionally one or both of these relationships is determined by curve-fitting, for example the respective relationship or relationships comprising a second or higher order polynomial function. Advantageously, the first relationship may further comprise a relationship between the first signal intensities and time (during reference gas measurement) and/or the second relationship may further comprise a relationship between the second signal intensities and time (during reference gas measurement).

In particular, a time A may be established within the first time period, at which a signal intensity for the first reference gas is the same as a signal intensity for the sample gas at time X. This may use the first relationship. A first reference isotope ratio for the time A may then be identified, also using the first relationship. A time B within the third time period may be established, at which a signal intensity for the second reference gas is the same as a signal intensity for the sample gas at time X. This may use the second relationship. Also using the second relationship, a second reference isotope ratio for the time B may be identified. Then, estimating the reference gas isotope ratio for the time X within the second measurement time period may be based on the first reference isotope ratio for the time A, the time A, the second reference isotope ratio for the time B and the time B. In other words, bracketing may be possible. This allows correcting for instrument drift, especially in LIDI IRMS.

In a more complex approach, for each of a plurality of first reference gas signal intensities (which are predicted signal intensities and therefore need not be the same as measured signal intensities for the first reference gas), a respective first reference isotope ratio, $R_{1,n}$, and a respective time $A_n$ within the first time period may be established, using the first relationship. In other words, the first relationship allows isotope ratios to be determined for signal intensities that have not been measured (for example, intensities between two measured intensities due to a limited number of measured intensity values). Moreover, for each of a plurality of second reference gas signal intensities (which need not be the same as measured signal intensities for the second reference gas), a respective second reference isotope ratio, $R_{2,n}$, and a respective time $B_n$ within the third time period may be established, using the second relationship. In particular, the determined relationship between the first isotope ratios and the first signal intensities and/or relationship between the first signal intensities and time may be used for the first reference isotope ratios, $R_{1,n}$, and respective times $A_n$ and the determined relationship between the second isotope ratios and the second signal intensities and/or relationship between the second signal intensities and time may be used for the second reference isotope ratios, $R_{2,n}$, and respective times $B_n$ within the third time period. One of the first reference gas signal intensities and one of the second reference gas signal intensities that are the same may each be selected. Then, estimating the reference gas isotope ratio for the time X within the second measurement time period may be based on the first reference isotope ratio for the selected first reference gas signal intensity, the time $A_n$ for the selected first signal intensity, the second reference isotope ratio for the selected second signal intensity and the time $B_n$ for the selected second signal intensity. Beneficially, the selected first reference gas signal intensity and the selected second reference gas signal intensity are the same as the measured sample gas signal intensity at the time X.

This approach may be extended for estimating reference gas isotope ratios at other times within the second time period. For example, a further one of the first reference gas signal intensities and a further one of the second reference gas second signal intensities that are the same may be selected. A reference gas isotope ratio for a time Y (different from the time X) within the second measurement time period may be estimated, based on the first reference isotope for the selected further first reference gas signal intensity, the time $A_n$ for the selected further first reference gas signal intensity, the second reference isotope ratio for the selected further second reference gas signal intensity and the time $B_n$ for the selected further second signal intensity.

In the preferred embodiment, estimating the reference gas isotope ratio for the time X within the second measurement time period comprises linear interpolation between the first reference isotope ratio and the second reference isotope ratio in accordance with the position of time X between the time for the first reference gas signal intensity and the time for the second reference gas signal intensity.

In particular, a starting first signal intensity may be selected for measuring the first isotope ratios and first signal intensities and a starting second signal intensity may be selected for measuring the second isotope ratios and second signal intensities. Advantageously, the starting first signal intensity and the starting second signal intensity need not be related to a starting signal intensity for the sample gas measurements and optionally, the starting first signal intensity and the starting second signal intensity may be the same. In other words, there may be less uncertainty regarding the pressure adjustment for the reference gas. In particular, the reference gas pressure may always be adjusted to the same value. There is no need for a precise adjustment of the reference gas starting intensity.

In an embodiment of the inventive method the reference gas starting intensity might be higher than the sample gas starting intensity. Then a reference isotope ratio for the sample gas at the beginning of its measurement, when its partial pressure and signal intensity has normally its maximum value, is defined more accurately by the relationship between the isotope ratio measured for the reference gas and its signal intensity. Preferably this is applied for both reference gas measurement periods.

One advantage of the techniques disclosed herein is that sample and reference capillary matching may be made significantly less demanding than for existing DI system systems. For example, the signal intensities for sample gas and reference gas may just be similar or overlap somewhat. In particular, a range of first signal intensities of the reference gas may be selected for measuring the first isotope ratios and first signal intensities and/or a range of second signal intensities of the reference gas may be selected for measuring the second isotope ratios and second signal intensities. The range of first signal intensities and/or the range of second signal intensities may be selected at least to overlap with a range of sample gas signal intensities measured over the second measurement time period. The overlap may be partial (in that the range for one or both of the reference gases may have a lower starting level and lower ending level than for the sample gas or may have a higher starting level and higher ending level than for the sample gas) or complete (in that the range for one or both of the reference gases may have a higher starting level and lower ending level than for the sample gas).

BRIEF DESCRIPTION OF THE DRAWINGS

The invention may be put into practice in a number of ways, and preferred embodiments will now be described by way of example only and with reference to the accompanying drawings, in which.

DETAILED DESCRIPTION OF PREFERRED EMBODIMENTS

Figure 1:
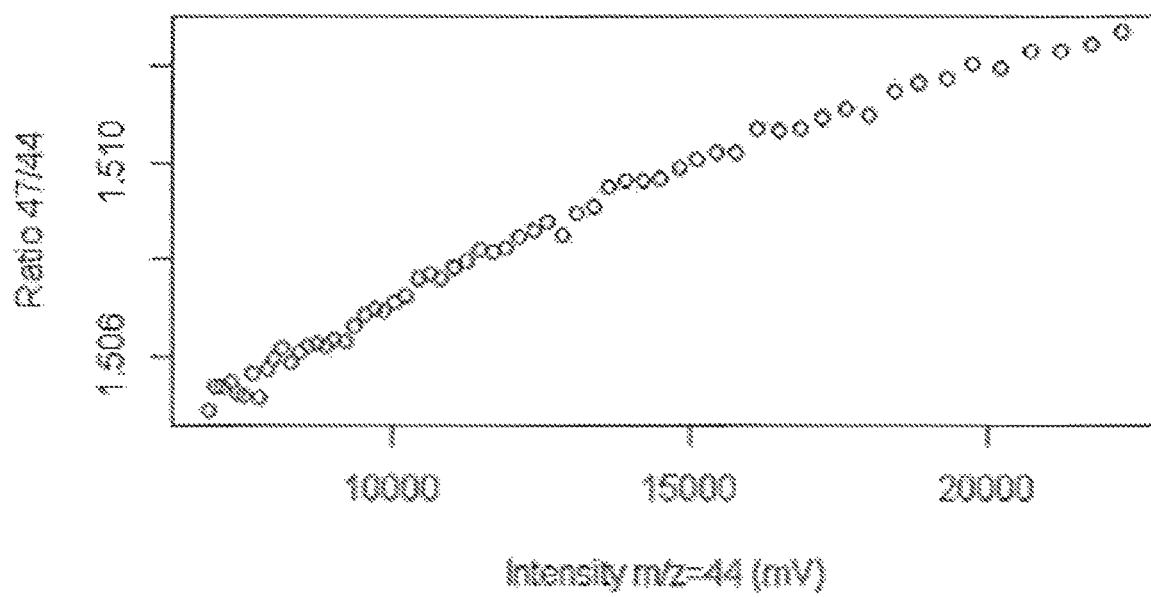
FIG. 1 shows an example plot of isotope ratios against signal intensity measurements.

Referring first to FIG. 1, there is shown an example plot of isotope ratios against signal intensity measurements for a LIDI IRMS system. In particular, this plot shows measured ratio of signals on mass 47 and 44 against signal intensity on mass 44 (in mV) for $CO_2$. Although the example of $CO_2$ measurement will be used for illustration, it is understood that measurement of other gases is possible. For existing IRMS systems, the measured ratio of the $^{13}C^{18}O^{16}O$ isotopologue to the $^{12}C^{16}O^{16}O$ isotopologue depends on signal intensity, which is related to the $CO_2$ pressure, due to the non-linearity of the IRMS system. In particular, changes in the conditions inside the ion source may mean that different isotope ratios are observed for the same gas, but at different gas pressures in the source. The different gas pressures are reflected by different signal intensities in this case.

For a DI system, such as a LIDI system, the reference gas and sample gas exhibit the same chemical composition. As a result, the non-linearity for both gases is the same. It has therefore been recognised that correcting a sample gas isotope ratio measured at a given beam intensity by the ratio of a reference gas measured at the same intensity will result in the same corrected isotope ratio, independent of the absolute intensity. In other words, by knowledge of the relationship between isotope ratios and signal intensity measurements for the reference gas, an estimate of an isotope ratio for the reference gas corresponding with the sample gas can be established. This can then be used to determine an isotope ratio of the sample gas in relation to the isotope ratio of the reference gas, expressed by a delta notation of the isotope ratio of the sample gas (against the reference gas as standard). Matching of sample gas and reference signal intensities may therefore be performed in post-processing, rather than at the time of measurement.

Knowledge of the relationships between isotope ratios and signal intensity measurements for the reference gas therefore allows determination of isotope ratios of the reference gas at the intensities of the sample gas at each time (in particular, an integration time interval) of the time period when the sample gas isotope ratio is measured. This can be extended to the case where that relationships change over time. By measuring the reference gas prior to and after the sample gas over a range of signal intensities of the reference gas, a pair of reference gas isotope ratios can be generated for each sample gas intensity measured with the same reference gas intensity. Any change of these two reference isotope ratios other than measurement uncertainty can be attributed to instrument drift occurring between the respective measurements of the reference gas. A linear drift may be assumed for the change of the reference gas isotope ratio assigned to a sample gas signal intensity. A hypothetical or estimated isotope ratio of the reference gas at the time of the sample measurement can thereby be calculated from the data of the measurements of the reference gas prior to and after the measurement of the sample gas and used to correct the sample isotope ratio. For the correction, the isotope ratio of the reference gas used is that determined for a signal intensity of the reference gas equal to the signal intensity of the sample gas at the time of the measurement of the isotope ratio of the sample gas.

In general terms, there may therefore be considered a method of operating an isotope ratio spectrometer (particularly, a dual inlet isotope ratio spectrometer) for measurement of a sample, comprising: measuring first isotope ratios and first signal intensities for a first reference in the spectrometer, over a first measurement time period, a first relationship comprising a relationship between the first isotope ratios and the first signal intensities being determined; measuring sample isotope ratios and sample signal intensities in the spectrometer, over a second measurement time period subsequent to the first measurement time period; measuring second isotope ratios and second signal intensities for a second reference in the spectrometer over a third measurement time period subsequent to the second measurement time period, a second relationship comprising a relationship between the second isotope ratios and the second signal intensities being determined; and estimating a reference isotope ratio for a time X within the second measurement time period, based on the first relationship and the second relationship. This reference isotope ratio is advantageously assigned to the signal intensity of the sample gas at the time X of measurement. Optionally, a sample fluid is generated (as a liquid and/or gas) from the sample and analysed to measure the sample isotope ratio and/or a reference fluid (as liquid and/or gas) is generated from the reference and analysed to measure the isotope ratio of the reference. The first and second references and the sample are preferably measured as gases. It should be noted that the first and second references are beneficially derived from the same source and have the same chemical composition.

The first relationship may allow an isotope ratio for any signal intensity of the first reference (preferably within or around a range of signal intensities measured for the first reference, for example within upper and lower limits of the range) to be determined. The second relationship may allow an isotope ratio for any signal intensity of the second reference (preferably within or around a range of signal intensities measured for the second reference, for example within upper and lower limits of the range) to be determined, for the third measurement time period. By comparing an isotope ratio for a specific signal intensity of the first reference given by the first relationship and an isotope ratio for the same specific signal intensity of the second reference given by the second relationship, an instrumental drift may be identified.

An alternative expression of this general sense may be as a method of operating an isotope ratio spectrometer (particularly, a dual inlet isotope ratio spectrometer) for measurement of a sample, comprising: measuring first isotope ratios and first signal intensities for a first reference in the spectrometer, over a first measurement time period in which the first signal intensity is varying, a first relationship comprising a relationship between the first isotope ratios and the first signal intensities being determined; measuring sample isotope ratios and sample signal intensities of the sample in the spectrometer, over a second measurement time period; and estimating a reference isotope ratio for a signal intensity of the first reference matching a measured sample signal intensity, using the first relationship. In other words, the relationship between the first isotope ratios and the first signal intensities may be used to establish an isotope ratio for the reference corresponding with any signal intensity (preferably within or around a range of signal intensities measured by the first measuring step, for example within upper and lower limits of the range). This relationship may be used to determine an isotope ratio of the reference for a signal intensity of the reference matching any of the signal intensities measured for the sample. This reference isotope ratio is advantageously assigned to the signal intensity of the sample gas at the time X of measurement. Optionally, a sample fluid is generated (as a liquid and/or gas) from the sample and analysed to measure the sample isotope ratio and/or a reference fluid (as liquid and/or gas) is generated from the reference and analysed to measure the isotope ratio of the reference. The first reference and the sample are preferably measured as gases.

The second measurement time period is preferably subsequent (and optionally directly subsequent) to the first measurement time period, but in less preferred approaches, the first measurement time period may be subsequent (and optionally directly subsequent) to the second measurement time period. Advantageously in accordance with the preferred approach, the method may further comprise measuring second isotope ratios and second signal intensities for a second reference in the spectrometer, over a third measurement time period subsequent to the second measurement time period, a second relationship comprising a relationship between the second isotope ratios and the second signal intensities being determined. Then, a reference isotope ratio may be estimated for a time X within the second measurement time period, based on the first relationship and the second relationship. Preferably for this the first isotope ratio and the second isotope ratio are used, which are defined by the first and second relationship, when the first and second signal intensity is matching the sample signal intensity at the time X. The second reference is preferably measured as a gas. It should be noted that the first and second references are beneficially derived from the same source and have the same chemical composition.

These methods and any other such method disclosed herein may be embodied as a computer program (for example on a computer readable medium, which may be non-transitory) or as an isotope ratio spectrometer (mass spectrometer or optical spectrometer, for example), configured to operate in accordance with the method. Other, potentially optional features and/or steps relevant to these methods will be discussed further below.

Preferably, the method further comprises normalizing one of the sample isotope ratios measured at the time X within the second measurement time period, using as estimated reference isotope ratio for the time X (for example to provide a "delta value" for the sample isotope ratio measured at the time X) that reference isotope ratio according to the determined first relationship for which the signal intensity of the reference matches (is equal to) the signal intensity of the sample at the time X. Optionally, the spectrometer is a LIDI isotope ratio spectrometer.

Specific implementation details for the procedure will now be described. Further reference in more general terms to the procedure of this disclosure will also be made below.

The measurement sequence will now be described, before discussing the data evaluation or processing steps. Sample and reference gases are present in reservoir, typically either a bellow (approximately 100 µL $CO_2$ at ambient pressure) or a micro-volume (approximately 20 µL $CO_2$ at ambient pressure). As described above, each sample gas measurement (typically lasting around 200 to 600 seconds and 300, 400 or 500 seconds being possible) is bracketed by a reference gas measurement beforehand and subsequently.

Capillaries delivering the sample gas and reference gas are typically matched by crimping as for classical DI measurements. However, the quality of the matching is significantly less demanding than for classical DI. It is desirable that the sample and reference intensities, which decrease during the measurement time periods of the LIDI measurement show a good overlap (for example, sample decay from 20000 to 11000 mV and reference decay from 25000 to 10000 mV, when the intensity is given by a voltage detected using a $10^8\Omega$ amplifier). A reduction of the gas pressure in the source and, hence, of signal intensity is inevitable. The decay rates may differ slightly, for instance about 1000 mV over 600 seconds on m/z 44, measured with a $10^8\Omega$ amplifier. This level of matching is acceptable, since the intensity matching is done during data evaluation or processing subsequently. The reference pressure is preferably not readjusted during measurement.

Reference gas measurements can each be performed using the same starting signal intensity. In other words, the starting intensity of the reference gas need not be matched to that of the sample. Each sequence begins and ends with a reference gas measurement, as noted above. In other words, each sequence comprises: a first measurement time period, in which the first reference gas is measured; a second measurement time period subsequent to (and preferably directly after, subject to preparation time, as discussed below) the first measurement time period, in which the sample gas is measured; and a third measurement time period subsequent to (and preferably directly after, again subject to preparation time) the second measurement time period, in which the second reference gas is measured. Both sample and reference gases are typically measured over 400 to 600 seconds (total integration time).

Additional time periods within the measurement process, specifically for preparation of the reference and sample gases depend on the way in which the instrument is used and operated. If measurements are made from the dual inlet, about 300 seconds additional delay is added between measurements (for flushing and pumping with gases, waiting for stabilization, etc.). If the common case of a sample preparation device (as discussed previously) is used, the sample gas (in this case, $CO_2$) is prepared from a carbonate mineral sample by acid digestion. Then, an additional period of between 1200 and 1800 seconds is added to each measurement time, resulting a total time per measurement period of 30 to 60 minutes. As a result, there can a relatively long delay between reference gas and sample gas measurements. It should be noted that a second reference gas measurement for a first sample gas may also be used as a first reference gas measurement for a second sample gas, measured after the first sample gas (provided the chemical compositions of the first sample gas and the second sample gas are the same).

The data evaluation procedure described next comprises two steps. First, the intensities of sample and reference are matched. This uses a determined relationship between measured isotope ratios and signal intensities for the reference gas measurements. In this way, a reference gas isotope ratio may be estimated for any signal intensity within the range of signal intensities measured. Classical DI measurements can benefit from the first step alone, as will be explained further below. Further drift correction may not be needed in that case. Moreover using two such relationships between measured isotope ratios and signal intensities for the reference gas measurements at different times, reference gas isotope ratios may further be estimated for any signal intensity within the range of signal intensities measured at any time between those different times. In a second step, particularly used for LIDI IRMS, two matched references are used to correct for instrumental drift using such a technique. These two steps will be discussed in more depth below.

Figure 2:
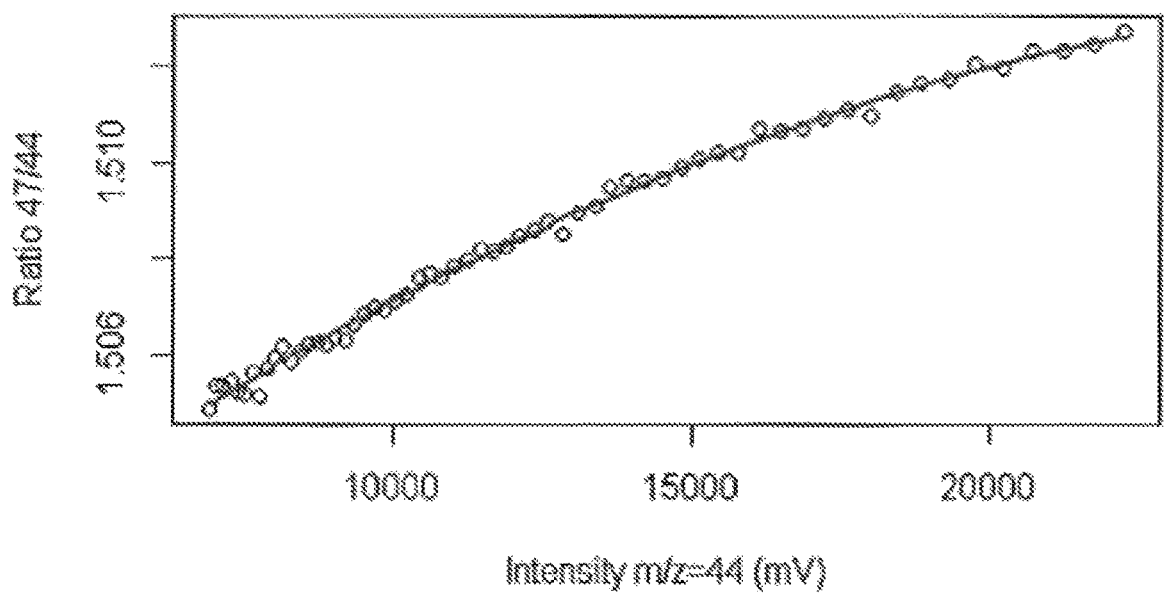
FIG. 2 shows the plot of FIG. 1 with a relationship between isotope ratios and signal intensity superimposed.

In the first step, "raw" reference isotope ratios are fitted to a model, such as a (mathematical) function. Referring next to FIG. 2, there is shown the plot of FIG. 1 with a relationship between isotope ratios and signal intensity superimposed. In this drawing, the measurements can be understood as being taken from a reference $CO_2$ gas. The signal intensities and "raw" reference gas isotope ratios were measured over time and the drawings shows (as in FIG. 1) a plot of the "raw" reference gas isotope ratios against the signal intensities for a single mass to charge (m/z) ratio. In this context, a "raw" isotope ratio may already include corrections such as pressure baseline and instrument background (for instance based on the sample measurement). The "raw" isotope ratio may also be calibrated. In FIGS. 1 and 2, the signal intensities are for a m/z ratio of 44, corresponding with the most common or main isotope for $CO_2$.

Using curve-fitting (interpolation, regression or smoothing), a suitable function is fitted to the measured ("raw") reference ratios against the signal intensity on one mass (in this case m/z ratio of 44). A suitable function can be a polynomial, particularly in this case (and as shown in FIG. 2), a second order polynomial. The function thereby defines a relationship between the isotope ratios and the signal intensities.

For the first reference gas measurements, this relationship is between the first isotope ratios and the first signal intensities (a first relationship) and for the second reference gas measurements, this relationship is between the second isotope ratios and the second signal intensities (a second relationship). The first and second relationships are likely to be similar in terms the type of curve fitted. However, the exact parameters of the curve may differ due to instrumental drift and/or changes in the environment in which the instrument was operating. As part of the first relationship, a relationship between the first signal intensities and time may also be determined. Similarly, as part of the second relationship, a relationship between the second signal intensities and time may also be determined.

The second step includes calculation of isotope ratios for one or more specific sample intensities. This step uses the functions (equations) resulting from the curve-fitting in the first step. In particular, a reference gas isotope ratio is calculated to correspond with a measured sample intensity at an integration time interval. Preferably, multiple reference gas isotope ratios are calculated, each corresponding with a respective measured sample intensity at an integration time interval.

Figure 3:
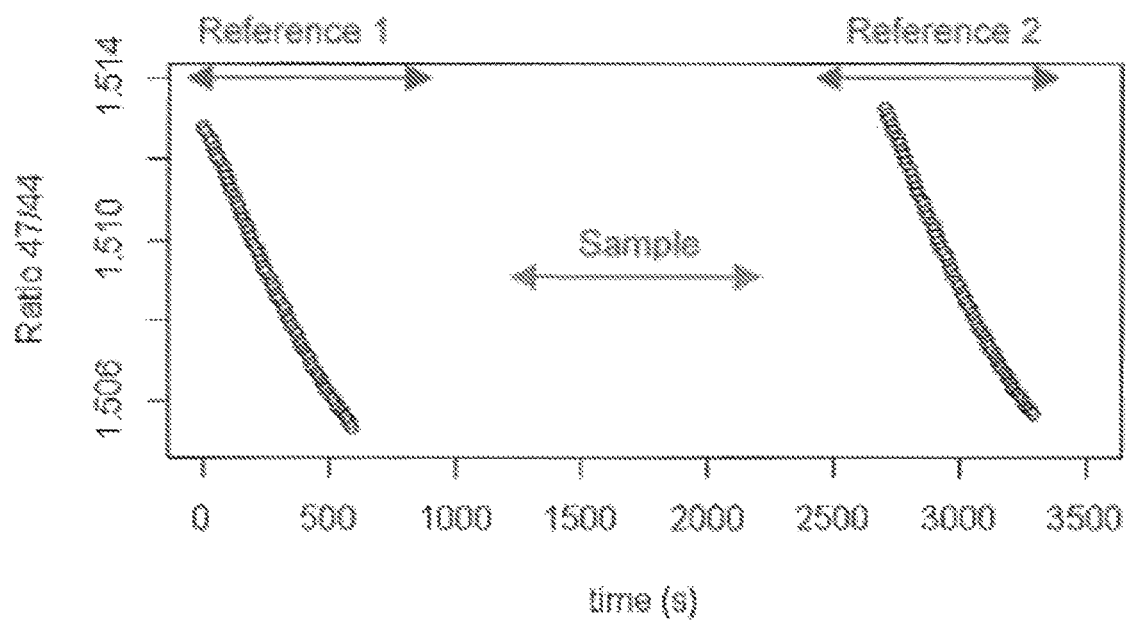
FIG. 3 depicts an example plot of isotope ratios against time based on reference gas measurement and derived relationships.

In this way, the reference isotope ratios can be transferred on a time scale. The distance between two consecutive reference ratios may correspond to the integration time interval of the sample. Moreover, the relative starting points of each reference run is known. Referring now to FIG. 3, there is depicted an example plot of isotope ratios against time based on reference gas measurement and derived relationships. This shows isotope ratios of the reference gas (between m/z ratios of 47 and 44) calculated for the given sample intensities from the respective first and second relationships as identified in the first step, plotted against their (hypothetical) measurement time, for example as identified from the relationships between signal intensities and time during reference gas measurements (as will be discussed further below). As a result, two sets of data points for reference gas isotope ratios are shown: one for the first reference gas measurement and one for the second reference gas measurement.

Figure 4:
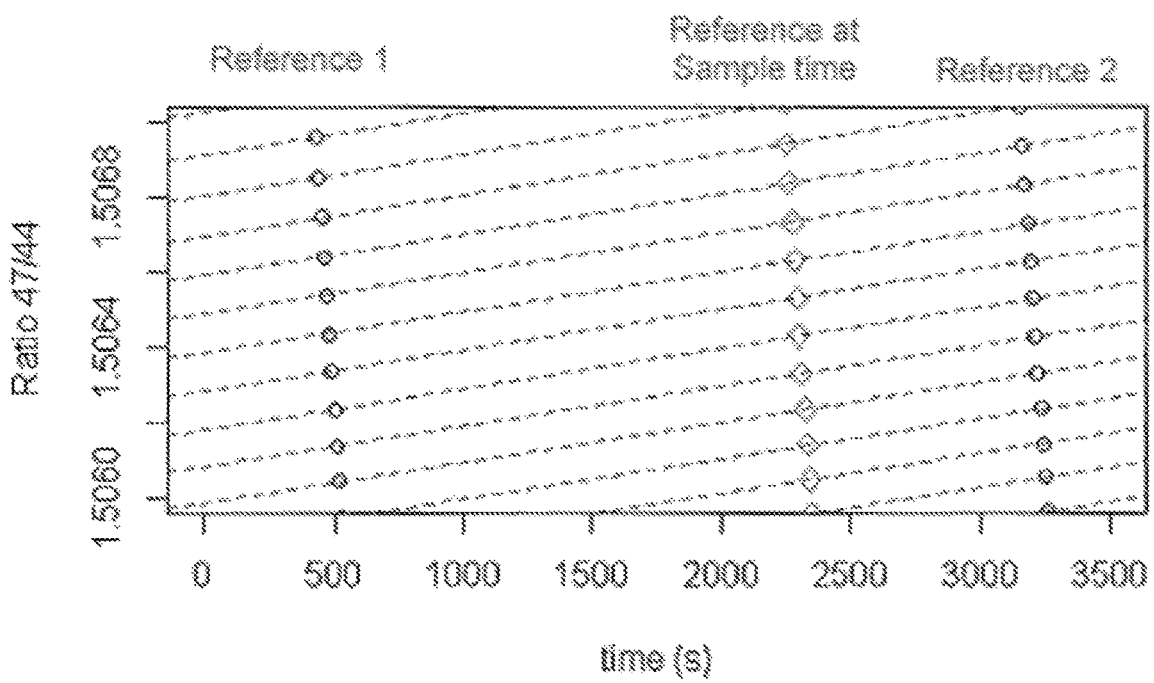
FIG. 4 schematically illustrates, on an example plot of isotope ratios against time in accordance with FIG. 3, derived relationships between isotope ratio against time and estimated isotope ratios for a reference gas during a sample gas measurement period.

These two sets of data points can then be used to determine instrument drift and perform bracketing. Referring now to FIG. 4, there is schematically illustrated, on an example plot of isotope ratios against time in accordance with FIG. 3, the determination of isotope ratios for a reference gas during a sample gas measurement period. In fact, FIG. 4 shows an expanded portion of the plot of FIG. 3, with dotted lines connecting a point in the first data set with a corresponding point in the second data set having the same signal intensity. Each dotted line represents a respective linear drift function, indicating a drift or change of the isotope ratio of the reference gas for a given signal intensity against time. In other words, for each pair of reference data points corresponding to the same intensity, a linear drift function may be calculated, between a first reference isotope ratio, $R_{1,n}$ at a time $A_n$ for the first reference gas and a second reference isotope ratio, $R_{2,n}$, a time $B_n$ for the second reference gas. Using this linear drift function, an isotope ratio for a reference gas can therefore be obtained at the time of the sample measurement with the same signal intensity, as shown by the diamond reference points in FIG. 4. These can be used to reference the sample accordingly. The referencing or normalization of the sample gas isotope ratio measurement ("delta" value calculations) are as well-known in this technical field and are simply performed using the reference isotope ratio calculated as described herein.

Due to the nonlinearity, the isotope ratio (for example, $^{13}C/^{12}C$) is a function of intensity ($I(^{44}CO_2)$). As long as the chemical composition of the sample and reference gases are the same, we can assume this function is the same for both gases. It will be appreciated from the foregoing that relationships between intensity measurement and time for the reference gas measurements are also desirably known. Within one LIDI sample cycle, the intensities on the respective masses are measured for a certain number of integration time intervals. A typical 600 second cycle consists of 60 such intervals of 10 seconds each. Typically over the measurement time period of the sample and reference gases, the intensity will decay, as indicated above.

Figure 5:
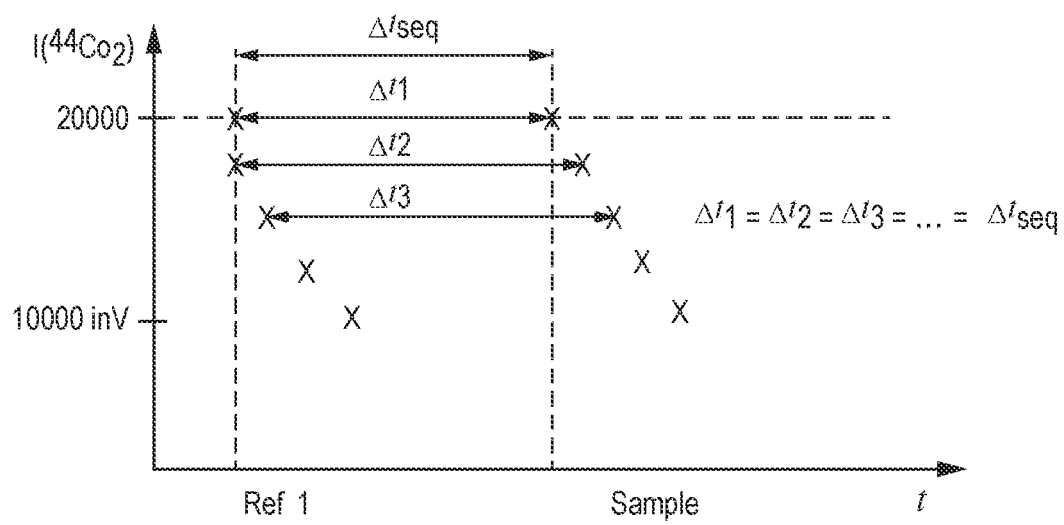
FIG. 5 plots intensity measurements for a reference gas and a sample gas against time in a first, more theoretical scenario.

With reference to FIG. 5, there are plotted intensity measurements for a reference gas and a sample gas against time in a first, more theoretical scenario. In this "ideal world" scenario, the decay of intensities for sample and reference would be exactly the same. As a consequence, if the starting intensity for the sample gas measurement and the starting intensity for a reference gas measurement were the same, the intensity measurement at each subsequent integration time interval for the sample gas would be the same as the intensity measurement at the respective integration time interval for the reference gas. This would allow use of the isotope ratios measured for the reference gas to correct the measurement of the sample gas, for each of the specific intensities. The time distance between the first reference gas measurement ("Ref. 1") and the sample gas measurement would be the same for each intensity and given by the respective starting times within the sequence (shown by $\Delta t_{seq}$ within FIG. 5).

Figure 6:
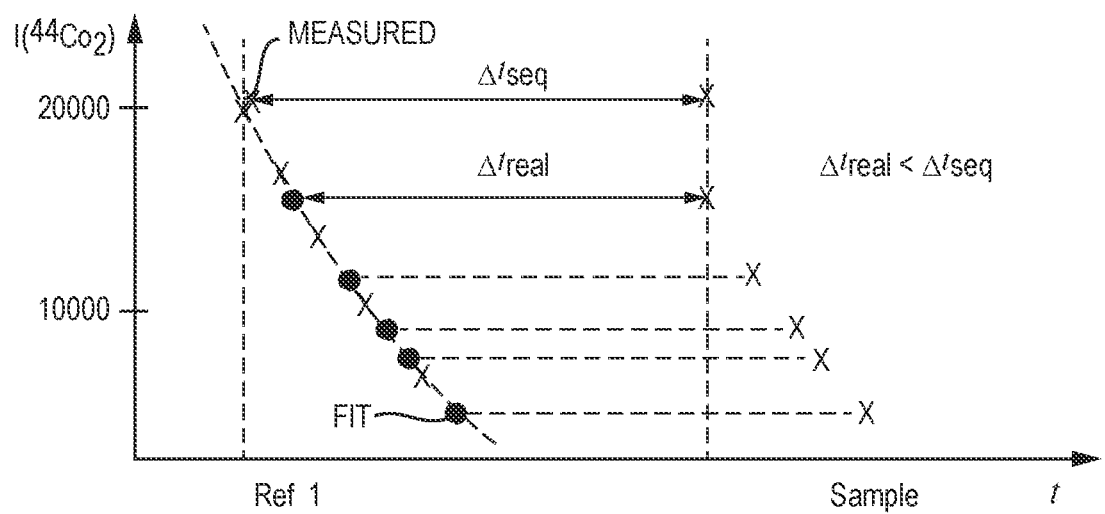
FIG. 6 depicts a plot of intensity measurements for a reference gas and a sample gas against time in a second, more realistic scenario

This more theoretical scenario is quite distanced from most practical embodiments. In reality and as explained above, the reference gas measurements are not made at the same intensities as the sample gas measurements. Rather, reference isotope ratios are calculated for the given sample intensities using fit functions. Nonetheless, use can still be made of the parameter $\Delta t_{seq}$ as described above, by assuming that the decay in intensity over time for the reference and sample gases is approximately the same. Referring now to FIG. 6, there is depicted a plot of intensity measurements for a reference gas and a sample gas against time in a second, more realistic scenario. In this scenario, the time difference between the first measurement of the first reference gas and the first measurement of the sample gas, $\Delta t_{seq}$, is determined. The time difference between the second measurement of the sample gas and the time at which the intensity of the first reference gas would have been the same, $\Delta t_{real}$, is shown. As shown in the drawing, $\Delta t_{real}$ is less than $\Delta t_{seq}$, if the starting intensity of the first reference gas measurement is higher than that of the sample gas. Contrastingly, if the starting intensity of the first reference gas measurement is lower than that of the sample gas, $\Delta t_{real}$ would be greater than $\Delta t_{seq}$. Both cases are equally likely.

On this basis, a simple model for reference gas signal intensity against time may assume that the time difference between a sample gas measurement and a first (preceding) reference gas measurement of the same signal intensity is a constant, $\Delta t_{seq}$. Similarly, a model of a constant time difference may be assumed between a sample gas measurement and a second (subsequent) reference gas measurement of the same signal intensity. The constant time difference may be based on the time difference between the first measurement of the sample gas and the first measurement of the second reference gas.

Such assumptions are essentially valid, particularly if the two *desiderata* discussed below are met.

1.) The crimping of the sample and reference capillaries should be similar, resulting in only marginal deviation in the signal decays. This is achievable with some effort, but need only be done once.
2.) The starting intensities for the reference and sample gases should be similar. If the intensity for the first reference gas would start significantly higher than for the sample gas, the assumed time offset would be longer than it actually is and vice versa. This may introduce some error. However, even considering atypically large fluctuations in the sample size, this error is less than 3 minutes. This can be neglected, given that the time difference between the first measurement of the first reference gas and the first measurement of the sample gas is up to 30 minutes, when using a sample preparation device, as discussed above.

In the general terms previously discussed, a relationship between the first signal intensities and time may be defined by a first reference starting time, at which an initial measurement of the first reference is made. A first time spacing may be defined by a difference between the first reference starting time and a time at which an initial measurement of the sample is made. Then, a time at which a specific signal intensity is considered for the first reference may be determined based on a time at which the specific signal intensity is measured for the sample and the first time spacing, in particular the time at which the specific signal intensity is measured for the sample reduced by the first time spacing.

A relationship between the second signal intensities and time may be defined by a second reference starting time, at which an initial measurement of the second reference is made. A second time spacing may be defined by a difference between the second reference starting time and a time at which an initial measurement of the sample is made. Then, a time at which a specific signal intensity is considered for the second reference may be determined based on a time at which the specific signal intensity is measured for the sample and the second time spacing, in particular the time at which the specific signal intensity is measured for the sample increased by the second time spacing.

Advantageously, the precision of the isotope ratio measurements for LIDI can significantly be improved. An improvement by a factor of two in precision appears to be readily obtainable and a factor of up to 10 in precision has been seen in experiments.

In the general terms identified above, this method may be described using a single first reference signal intensity and a single second reference signal intensity matched to a single sample intensity measurement. The method may therefore further comprise establishing a time A within the first time period, at which a signal intensity for the first reference is the same as a signal intensity for the sample at time X and thereby identify a first reference isotope ratio for the time A, using the first relationship. In addition, the method may comprise establishing a time B within the third time period, at which a signal intensity for the second reference is the same as a signal intensity for the sample at time X and thereby identify a second reference isotope ratio for the time B, using the second relationship. The reference isotope ratio for the time X within the second measurement time period may be estimated based on the first reference isotope ratio for the time A, the time A, the second reference isotope ratio for the time B and the time B.

In these general terms, the method may also be described for multiple first reference signal intensities and multiple second reference signal intensities. For example, the method may further comprise establishing, for each of a plurality of first reference signal intensities, a respective first reference isotope ratio, $R_{1,n}$, and a respective time $A_n$ within the first time period, using the first relationship. In addition, the method may comprise establishing, for each of a plurality of second reference signal intensities, a respective second reference isotope ratio, $R_{2,n}$, and a respective time $B_n$ within the third time period, using the second relationship. The value of n may range from 1 to N, where N is the number of signal intensities used (which may match the number of sample gas measurements made). One of the first reference signal intensities and one of the second reference signal intensities that are the same may be selected. The reference isotope ratio for the time X within the second measurement time period may be estimated based on the first reference isotope ratio for the selected first reference signal intensity, the time $A_n$ for the selected first signal intensity, the second reference isotope ratio for the selected second signal intensity and the time $B_n$ for the selected second signal intensity. The selected first reference signal intensity and selected second reference signal intensity advantageously match the measured sample signal intensity at the time X.

This may be repeated for multiple times within the second measurement time period. A further one of the first reference signal intensities and a further one of the second reference second signal intensities that are the same may be selected and a reference isotope ratio for a time Y within the second measurement time period (different from the time X) may be estimated based on the first reference isotope ratio for the selected further first reference signal intensity, the time $A_n$ for the selected further first reference signal intensity, the second reference isotope ratio for the selected further second reference signal intensity and the time $B_n$ for the selected further second signal intensity. The selected further first reference signal intensity and selected further second reference signal intensity advantageously match the measured sample signal intensity at the time Y. The same procedure may be repeated for further times Z within the second measurement time period, to allow selection of a first reference signal intensity and a second reference signal intensity matching the measured sample signal intensity at each time Z.

In the preferred embodiment, estimating the reference isotope ratio for the time X within the second measurement time period comprises linear interpolation between the first reference isotope ratio and the second reference isotope ratio, particularly in accordance with the position of time X between the time for the first reference signal intensity and the time for the second reference signal intensity.

Advantageously, the first relationship further comprises a relationship between the first signal intensities and time and/or wherein the second relationship further comprises a relationship between the second signal intensities and time. Additionally or alternatively, the relationship between the first isotope ratios and the first signal intensities and/or the relationship between the second isotope ratios and the second signal intensities comprise a second or higher order polynomial function.

In embodiments, the step of measuring first isotope ratios and first signal intensities for the first reference comprises selecting a starting first signal intensity, wherein the step of measuring second isotope ratios and second signal intensities for the second reference comprises selecting a starting second signal intensity. Then, the starting first signal intensity and the starting second signal intensity may be substantially the same (within normal measurement bounds). Additionally or alternatively, the step of measuring first isotope ratios and first signal intensities for the first reference comprises selecting a range of first signal intensities, wherein the step of measuring second isotope ratios and second signal intensities for the second reference comprises selecting a range of second signal intensities. Then, the range of first signal intensities and/or the range of second signal intensities may be selected at least to overlap with a range of sample signal intensities measured over the second measurement time period. Preferably, the sample and/or reference are provided as fluids (most preferably, gases) from a reservoir comprising a finite volume. Additionally or alternatively, the sample and/or reference fluids are generated from a sample, a liquid or solid sample for example, in a sample preparation device and then the sample and/or reference fluids are analysed.

Figure 7:
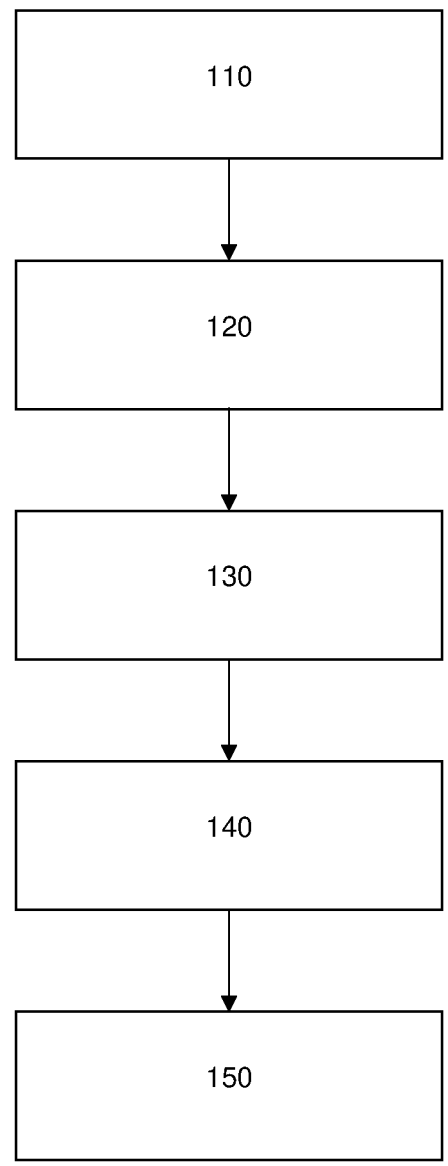
FIG. 7 shows a flowchart of a process for operating an isotope ratio spectrometer for measurement of a sample gas, in accordance with the disclosure.

Referring now to FIG. 7, there is shown a flowchart of a process for operating an isotope ratio spectrometer for measurement of a gaseous sample, in accordance with the disclosure. In first reference gas measurement step 110, first isotope ratios and first signal intensities are measured for a first reference gas in a IRMS. The first reference gas measurement step 110 is performed over a first measurement time period. In sample gas measurement step 120, sample gas isotope ratios and sample gas signal intensities are measured for a sample gas in the IRMS. This is performed over a second measurement time period, subsequent to the first measurement time period. In second reference gas measurement step 130, second isotope ratios and second signal intensities are measured for a second reference gas in the IRMS. This is performed over a third measurement time period subsequent to the second measurement time period. The first and second reference gases and the sample gas all comprise the same constituent type of gas.

In relationship determination step 140, a first relationship, comprising a relationship between the first isotope ratios and the first signal intensities, and a second relationship, comprising a relationship between the second isotope ratios and the second signal intensities are determined. Then, in reference estimation step 150, a reference gas isotope ratio for a time X within the second measurement time period is estimated, based on the first relationship and the second relationship. Reference estimation step 150 can be repeated for multiple times using the same first relationship and the second relationship. The whole process can be repeated for multiple different sample gases (which may comprise the same constituent type of gas or different types of gas).

It will be appreciated that variations to the foregoing design can be made while still falling within the scope of the disclosure. For example, the sample and reference gas need not be $CO_2$. Any gas with known isotopic variants can be used. The structure of the IRMS system and/or measurement technique may also differ from that disclosed herein. Optical spectroscopy or mass spectrometry may be used. Linear interpolation between the first reference isotope ratio and the second reference isotope ratio is used for estimating the reference gas isotope ratio to be used for referencing the sample gas isotope ratio is the method described above, but the skilled person will understand that alternatives may be possible in accordance with different models of instrument drift and/or environmental changes.

The technique of this disclosure may be applied to classical DI IRMS. In classical DI IRMS, the volume of the sample gas in classical DI is typically more than sufficient for a measurement of the sample gas with the desired precision. A typical measurement procedure for such instruments is described below, although it will be appreciated that variations are possible within this technique.

(1) The sample gas is directed into the IRMS analyser. The available intensity with the sample gas is determined.
(2) The reference gas intensity (the partial pressure in the ion source) is adjusted to match the sample intensity.
(3) A reference gas measurement is started for a first cycle (integration time). During steps (2) and (3), the sample gas flow is not stopped, but diverted to a vacuum. In other words, the sample gas volume is depleted during these steps.
(4) Next, the DI IRMS instrument is set back to the sample measurement mode and the sample gas is again measured. During this time, the reference gas is diverted to vacuum.
(5) Steps (3) and (4) are repeated as long as desired, required or possible, typically for around 10 sample cycles and 11 reference cycles. The last cycle is always a reference measurement.

Bracketing for classical DI measurements has typically been achieved in a different way to that described above. For n cycles of sample gas measurement, there are n+1 cycles of reference gas measurement and typically a single integration time interval per measurement (which contrasts with existing LIDI approaches, in which there are typically the same number of sample gas and reference gas measurements and/or multiple integration time intervals per measurement). For each cycle, there is one average intensity per mass (or mass-to-charge ratio), for example as indicated in the table below for five cycles.

| | Sample Intensities (mV) | | | | Reference Intensities (mV) | | | |
|---|---|---|---|---|---|---|---|---|
| Cycle | Mass 44 | Mass 45 | Mass 46 | Mass 47 | Mass 44 | Mass 45 | Mass 46 | Mass 47 |
| 1 | — | — | — | — | 12345 | 23456 | 34567 | 45678 |
| 2 | 12346 | 23457 | 34568 | 45679 | — | — | — | — |
| 3 | — | — | — | — | 10345 | 20456 | 30567 | 40678 |
| 4 | 10346 | 20457 | 30568 | 40679 | — | — | — | — |
| 5 | — | — | — | — | 9345 | 8456 | 7567 | 5678 |

As with LIDI measurement, there is some decay of the intensities along the cycles. In order to correct for the resulting non-linearity and instrument drift, the sample intensities are now transferred onto the delta scale using the average of the previous and succeeding reference intensity, as shown in the table below with the additional estimated reference intensities added for cycles 2 and 4, in which the sample intensities were measured.

| | Sample Intensities (mV) | | | | Reference Intensities (mV) | | | |
|---|---|---|---|---|---|---|---|---|
| Cycle | Mass 44 | Mass 45 | Mass 46 | Mass 47 | Mass 44 | Mass 45 | Mass 46 | Mass 47 |
| 1 | — | — | — | — | 12345 | 23456 | 34567 | 45678 |
| 2 | 12346 | 23457 | 34568 | 45679 | 11345 | 21956 | 32567 | 43178 |
| 3 | — | — | — | — | 10345 | 20456 | 30567 | 40678 |
| 4 | 10346 | 20457 | 30568 | 40679 | 9845 | 14456 | 19067 | 23178 |
| 5 | — | — | — | — | 9345 | 8456 | 7567 | 5678 |

Taking an average assumes that the sample gas measurement time periods and reference gas measurement time periods were of the same duration and at intervals of the same length of time. If either or both assumptions do not apply, linear interpolation can be used instead.

There are two significant differences between classical DI and LIDI measurements. Firstly, the measurement time per cycle for DI is shorter (approximately 10 to 30 second for classical DI). As a consequence, the decay in two subsequent reference measurements is negligible. This allows averaging or linear interpolation of the intensities, without the need to identify a non-linear relationship between isotope ratios and reference gas intensities. Secondly, the intensity for LIDI measurements typically decreases by around 10000 mV during the cycle. This effectively excludes averaging intensities.

However, if a pronounced decay in the intensities during sample and/or reference measurement is present for classical DI, application of the method of the present disclosure would potentially improve the precision and accuracy of the data obtained. For example, this might occur with a classical DI measurement using a medium integration time interval (for instance, 30 seconds). This might be considered as sequence of LIDI measurements, but for one single sample. In classical DI, there is at least one sample measurement (with at least one integration time interval) and at least two reference measurements per sample measurement. The procedures for intensity matching and bracketing could be applied to such classical DI using all sample and reference cycles from one sample.

As mentioned previously, the techniques disclosed herein can be applied to measurements of gases other than $CO_2$, for example, $CH_4$ or $N_2O$. Apart from considering different isotope ratios, no changes would be needed.

A simple model for reference gas signal intensity against time of a constant time difference between the sample gas measurement and a reference gas measurement of the same intensity has been assumed above. However, improvements to this model are possible. The simple model introduces some error, by assuming a constant time difference between measurement of reference and sample gases of the same intensity. Improvement to this model may include application a correction factor. However, it is envisaged that such a correction factor would be small if the *desiderata* above are implemented. Otherwise, the correction factor could take account of any difference from those *desiderata*.

Another variation may be in the way that the reference gas measurement is made. A currently preferred approach is to match the initial signal intensity of the reference gas to that of the previous sample gas measurement. Especially with a sample preparation device of the type discussed earlier, this appears to work well. Due to the laborious sample preparation, the previous sample gas measurement is closer in time to this reference gas measurement. However, alternatives can be considered. A first option would be to measure the reference gas over a broad, fixed range of its signal intensity (such as from 25 V down to 8 V). This would have the advantage that the signal intensities for the reference gas would cover the range of the sample in any case.

A second approach would be to determine the quantity of sample gas before the first reference gas measurement is made and then adjust the starting intensity for the first reference gas accordingly. One example for achieving this would be by use of an electronic pressure sensor, for example within the sample preparation device. The first reference gas would then be adjusted based on this determination using some calibration function. The sequence of measurements for multiple sample gases would potentially get more complex, because a distinct first and second reference gas measurement would be required for each sample gas. In other words, a second reference gas measurement for a first sample gas would not be used as a first reference gas measurement for a second sample gas, measured after the first sample gas. Rather, the sequence would follow: first reference gas measurement; sample gas measurement; second reference gas measurement; first reference gas measurement; sample gas measurement; second reference gas measurement; etc. An advantage of this approach would be potentially perfect physical intensity matching. It is not clear if this would improve the resulting data quality, but throughput may be reduced accordingly.

In the approaches discussed above, each sample gas measurement is directly preceded and directly followed by a reference gas measurement. Assuming the drift is constant over a sufficient period of time, the number of references may be reduced, effectively resulting in a sequence: first reference gas measurement; first sample gas measurement; second sample gas measurement; third sample gas measurement; second reference gas measurement; fourth sample gas measurement; etc. Each sample gas measurement may be referenced by the reference gas measurements preceding and following it. Potentially, this could increase throughput. However, use of a sample preparation device may mean that the sample preparation makes the largest contribution to any throughput limit. Therefore, such an approach may not have a significant effect.

Although the reference gas measurement typically concerns a gas for use in providing an isotope ratio of the sample using the delta notation, alternatives are possible. For example, the measurement of isotope ratios for (solid) carbonates may be carried out by referencing the measurement to that of another carbonate that is an accepted standard reference material (SRM), for example NBS-19 by the International Atomic Energy Agency (IAEA). Under a current approach (for practical reasons), the samples are still referenced against a reference gas in the first step. The SRMs are measured in parallel, using the same sample preparation unit and against the same reference gas. In evaluation, the SRM measurements are then used to calibrate the reference gas measurements and, thereby, the delta notation isotope ratio for the sample gas is linked to the SRM measurement.

An alternative approach based on the approach in the present disclosure makes it possible to omit the reference gas measurements completely. Rather than measuring a reference gas and a SRM in parallel, it would be possible to measure the SRM only (which would then effectively be a reference) before and after each carbonate sample, in a sequence, with no gases in between. The intensity matching of the present application would allow direct referencing of the samples with the SRM. Bracketing could still be used for drift correction (and this would be advantageous if instrument drift is a factor). Then, the number of SRMs in-between would probably higher than with the current procedure. As a result, this approach may only make sense with a very stable IRMS, not requiring regular drift correction.

Although the invention has been described with reference to particular types of device and applications (particularly LIDI IRMS) and the invention has particular advantages in such case, as discussed herein, the invention may be applied to other types of device and/or application, for example classical DI IRMS as described. Also, whilst it will be understood that gases are analysed in the preferred embodiment, but other fluids could additionally or alternatively be analysed. Each feature disclosed in this specification, unless stated otherwise, may be replaced by alternative features serving the same, equivalent or similar purpose. Thus, unless stated otherwise, each feature disclosed is one example only of a generic series of equivalent or similar features.

As used herein, including in the claims, unless the context indicates otherwise, singular forms of the terms herein are to be construed as including the plural form and vice versa. For instance, unless the context indicates otherwise, a singular reference herein including in the claims, such as "a" or "an" (such as a gaseous sample) means "one or more" (for instance, one or more gaseous samples). Throughout the description and claims of this disclosure, the words "comprise", "including", "having" and "contain" and variations of the words, for example "comprising" and "comprises" or similar, mean "including but not limited to", and are not intended to (and do not) exclude other components.

The use of any and all examples, or exemplary language ("for instance", "such as", "for example" and like language) provided herein, is intended merely to better illustrate the invention and does not indicate a limitation on the scope of the invention unless otherwise claimed. No language in the specification should be construed as indicating any non-claimed element as essential to the practice of the invention.

Any steps described in this specification may be performed in any order or simultaneously unless stated or the context requires otherwise.

All of the aspects and/or features disclosed in this specification may be combined in any combination, except combinations where at least some of such features and/or steps are mutually exclusive. As described herein, there may be particular combinations of aspects that are of further benefit, such the aspects of curve fitting and/or interpolation for LIDI IRMS. In particular, the preferred features of the invention are applicable to all aspects of the invention and may be used in any combination. Likewise, features described in non-essential combinations may be used separately (not in combination).

The invention claimed is:

1. A computer program product including one or more non-transitory computer-readable media having computer program instructions stored therein, the computer program instructions being configured such that, when executed by one or more computing devices, cause the one or more computing devices to perform the steps of:
measuring first isotope ratios and first signal intensities for a first reference in the spectrometer, over a first measurement time period, a first relationship comprising a relationship between the first isotope ratios and the first signal intensities being determined;
establishing a time A within the first time period, at which a signal intensity for the first reference is considered the same as a signal intensity for the sample at time X and thereby identify a first reference isotope ratio for the time A, using the first relationship;
measuring sample isotope ratios and sample signal intensities in the spectrometer, over a second measurement time period subsequent to the first measurement time period;
measuring second isotope ratios and second signal intensities for a second reference in the spectrometer, over a third measurement time period subsequent to the second measurement time period, a second relationship comprising a relationship between the second isotope ratios and the second signal intensities being determined;
establishing a time B within the third time period, at which a signal intensity for the second reference is the considered same as a signal intensity for the sample at time X and thereby identify a second reference isotope ratio for the time B, using the second relationship; and
estimating a reference isotope ratio for a time X within the second measurement time period, based on the first relationship and the second relationship, wherein estimating the reference isotope ratio for the time X within the second measurement time period is based on the first reference isotope ratio for the time A, the time A, the second reference isotope ratio for the time B and the time B.

2. The computer program product of claim 1, further comprising:
establishing, for each of a plurality of first reference signal intensities, a respective first reference isotope ratio, $R_{1,n}$, and a respective time $A_n$ within the first time period, using the first relationship; and
establishing, for each of a plurality of second reference signal intensities, a respective second reference isotope ratio, $R_{2,n}$ and a respective time $B_n$ within the third time period, using the second relationship;
selecting one of the first reference signal intensities and one of the second reference signal intensities that are the same; and
wherein estimating the reference isotope ratio for the time X within the second measurement time period is based on the first reference isotope ratio for the selected first reference signal intensity, the time $A_n$ for the selected first signal intensity, the second reference isotope ratio for the selected second signal intensity and the time $B_n$ for the selected second signal intensity.

3. The computer program product of claim 2, wherein the selected first reference signal intensity and the selected second reference signal intensity are the same as the measured sample signal intensity at the time X.

4. The computer program product of claim 3, further comprising:
selecting a further one of the first reference signal intensities and a further one of the second reference second signal intensities that are the same; and
estimating a reference isotope ratio for a time Y within the second measurement time period, different from the time X, based on the first reference isotope for the selected further first reference signal intensity, the time $A_n$ for the selected further first reference signal intensity, the second reference isotope ratio for the selected further second reference signal intensity and the time $B_n$ for the selected further second signal intensity.

5. The computer program product of claim 3, wherein estimating the reference isotope ratio for the time X within the second measurement time period comprises linear interpolation between the first reference isotope ratio and the second reference isotope ratio in accordance with the position of time X between the time for the first reference signal intensity and the time for the second reference signal intensity.

6. The computer program product of claim 1, wherein the first relationship further comprises a relationship between the first signal intensities and time and/or wherein the second relationship further comprises a relationship between the second signal intensities and time.

7. The computer program product of claim 1, wherein the relationship between the first isotope ratios and the first signal intensities and/or the relationship between the second isotope ratios and the second signal intensities comprise a linear function or a second or higher order polynomial function.

8. The computer program product of claim 1, wherein the step of measuring first isotope ratios and first signal intensities for the first reference comprises selecting a starting first signal intensity, wherein the step of measuring second isotope ratios and second signal intensities for the second reference comprises selecting a starting second signal intensity and wherein the starting first signal intensity and the starting second signal intensity are the same.

9. The computer program product of claim 1, wherein the step of measuring first isotope ratios and first signal intensities for the first reference comprises selecting a range of first signal intensities, wherein the step of measuring second isotope ratios and second signal intensities for the second reference comprises selecting a range of second signal intensities and/or wherein the range of first signal intensities and/or the range of second signal intensities are selected at least to overlap with a range of sample signal intensities measured over the second measurement time period.

10. The computer program product of claim 1, further comprising:
normalizing one of the sample isotope ratios measured at the time X within the second measurement time period, using the estimated reference isotope ratio for the time X.

11. The computer program product of claim 1, wherein the spectrometer is a Long Integration Dual Inlet (LIDI) isotope ratio spectrometer.

12. The computer program product of claim 1 wherein a sample fluid is generated from the sample in a sample preparation device and then the generated sample fluid is analysed to measure the isotope ratio of the sample and/or a reference fluid is generated in a reference preparation device and then the generated reference fluid is analysed to measure the isotope ratio of the reference.

13. An isotope ratio spectrometer system comprising:
an isotope ratio spectrometer;
one or more processors; and
one or more non-transitory computer-readable media having computer program instructions stored therein, the computer program instructions being configured such that, when executed by one or more processors, the one or more processors cause the performance of the steps of:
  measuring first isotope ratios and first signal intensities for a first reference in the spectrometer, over a first measurement time period, a first relationship comprising a relationship between the first isotope ratios and the first signal intensities being determined;
  establishing a time A within the first time period, at which a signal intensity for the first reference is considered the same as a signal intensity for the sample at time X and thereby identify a first reference isotope ratio for the time A, using the first relationship;
  measuring sample isotope ratios and sample signal intensities in the spectrometer, over a second measurement time period subsequent to the first measurement time period;
  measuring second isotope ratios and second signal intensities for a second reference in the spectrometer, over a third measurement time period subsequent to the second measurement time period, a second relationship comprising a relationship between the second isotope ratios and the second signal intensities being determined;
  establishing a time B within the third time period, at which a signal intensity for the second reference is the considered same as a signal intensity for the sample at time X and thereby identify a second reference isotope ratio for the time B, using the second relationship; and
  estimating a reference isotope ratio for a time X within the second measurement time period, based on the first relationship and the second relationship, wherein estimating the reference isotope ratio for the time X within the second measurement time period is based on the first reference isotope ratio for the time A, the time A, the second reference isotope ratio for the time B and the time B.

14. The isotope ratio spectrometer system of claim 13, wherein the computer program instructions further cause the one or more processors to further cause the performance of the steps:
  establishing, for each of a plurality of first reference signal intensities, a respective first reference isotope ratio, $R_{1,n}$, and a respective time $A_n$ within the first time period, using the first relationship; and
  establishing, for each of a plurality of second reference signal intensities, a respective second reference isotope ratio, $R_{2,n}$, and a respective time $B_n$ within the third time period, using the second relationship;
  selecting one of the first reference signal intensities and one of the second reference signal intensities that are the same; and
  wherein estimating the reference isotope ratio for the time X within the second measurement time period is based on the first reference isotope ratio for the selected first reference signal intensity, the time $A_n$ for the selected first signal intensity, the second reference isotope ratio for the selected second signal intensity and the time $B_n$ for the selected second signal intensity.

15. The isotope ratio spectrometer system of claim 14, the selected first reference signal intensity and the selected second reference signal intensity are the same as the measured sample signal intensity at the time X.

16. The isotope ratio spectrometer system of claim 15, wherein the computer program instructions further cause the one or more processors to further cause the performance of the steps:
  selecting a further one of the first reference signal intensities and a further one of the second reference second signal intensities that are the same; and
  estimating a reference isotope ratio for a time Y within the second measurement time period, different from the time X, based on the first reference isotope for the selected further first reference signal intensity, the time $A_n$ for the selected further first reference signal intensity, the second reference isotope ratio for the selected further second reference signal intensity and the time $B_n$ for the selected further second signal intensity.

17. The isotope ratio spectrometer system of claim 15, wherein estimating the reference isotope ratio for the time X within the second measurement time period comprises linear interpolation between the first reference isotope ratio and the second reference isotope ratio in accordance with the position of time X between the time for the first reference signal intensity and the time for the second reference signal intensity.

18. The isotope ratio spectrometer system of claim 14, wherein the first relationship further comprises a relationship between the first signal intensities and time and/or wherein the second relationship further comprises a relationship between the second signal intensities and time.

* * * * *